United States Patent [19]  [11] 4,117,023
Gillet et al.  [45] Sep. 26, 1978

[54] METHOD OF SEPARATION OF CATALYTIC RESIDUES DERIVED FROM ALUMINUM CHLORIDE

[75] Inventors: Philippe Jean Gillet, Creutzwald; Gaston Henrich, Saint-Avold, both of France

[73] Assignee: Societe Chimique des Charbonnages, Courbevoie, France

[21] Appl. No.: 741,488

[22] Filed: Nov. 12, 1976

[30] Foreign Application Priority Data

Nov. 13, 1975 [FR] France ................................. 75 34703
Nov. 13, 1975 [FR] France ................................. 75 34704

[51] Int. Cl.$^2$ ........................... C07C 3/56; C07C 7/00
[52] U.S. Cl. .............................. 260/671 R; 260/671 B; 260/671 P; 260/674 A; 260/674 R
[58] Field of Search ............ 260/674 R, 674 A, 671 R, 260/671 P, 671 B

[56] References Cited

U.S. PATENT DOCUMENTS

| | | | |
|---|---|---|---|
| 2,376,088 | 5/1945 | Robinson | 260/671 R |
| 3,499,054 | 3/1970 | Resh et al. | 260/674 A |
| 3,679,770 | 7/1972 | Nicolet | 260/671 P |
| 3,703,559 | 11/1972 | Kerfoot et al. | 260/674 A |

Primary Examiner—Delbert E. Gantz
Assistant Examiner—C. E. Spresser
Attorney, Agent, or Firm—Karl W. Flocks

[57] ABSTRACT

The present invention relates to an improved method of separation of the mineral salts obtained from the catalyst of a Friedel-Craft reaction.

The improvement to the method of alkylation of an aromatic hydrocarbon by an olefin hydrocarbon in the presence of aluminum chloride followed by neutralization of the acid alkylates by anhydrous ammonia, consists in flocculating the mineral salts obtained by said neutralization by the addition of water and separating out the salts thus flocculated.

9 Claims, No Drawings

METHOD OF SEPARATION OF CATALYTIC RESIDUES DERIVED FROM ALUMINUM CHLORIDE

The present invention relates to a method of separation of the mineral salts obtained from the catalyst of a Friedel-Craft reaction.

It is known that the Friedel-Craft reaction is utilized industrially, especially in the manufacture of ethyl-benzene from ethylene and benzene, of cumene from propylene and benzene, and cymenes from toluene and propylene. After alkylation, these are separated out by decantation, on the one hand alkylates containing a certain quantity of dissolved catalytic complex, and on the other hand a catalytic complex known as "red oil", the composition of which represents one third mineral matter (aluminum salts, HCl) and two thirds hydrocarbons. The alkylates are usually treated with a base such as soda or ammonia, and then with water, and again, if desired with soda, which has the disadvantage of causing alkylates to be carried away in the washing solutions, and resulting in losses and possibly the soiling by the solutions carried away of the streams of water in which the rejects of these solutions are removed.

More recently it has been discovered that it was possible to neutralize the acid alkylates after decantation of the complex by anhydrous ammonia, preferably in the gaseous form, which avoids pollution of the discharge water and less of alkylates in this water.

After this treatment there is obtained, in suspension in the alkylate, a mixture of salts composed of aluminum chloride and a complex resulting from the action of ammonia on $AlCl_3$.

The separation of the mixture of salts obtained can be effected by decantation, but the time to obtain sufficient decantation is very slow, of the order of 36 to 80 hours, and represents a prohibitive cost for a commercial product. Centrifugation gives more rapid results, but it necessitates installations of very large size when it is desired to treat large quantities of alkylates, and the result obtained is frequently insufficient. As regards filtration, this is also expensive and difficult to apply when it is a matter of treating the very large quantities obtained in modern installations for the synthesis of ethyl-benzene for the manufacture of styrene or cumene for the preparation of phenol.

The Applicants have discovered that it is possible to obtain rapid and complete decantation by the addition of a small quantity of water to the medium. According to the invention, therefore, flocculation of the salts of an alkylate neutralized by anhydrous ammonia is effected by adding a sufficient quantity of water to the stirred medium and decanting the salts at the lower part of the apparatus (bottom): the quantity of water added represents preferably 15 to 20% of the dry salts.

According to a preferred method of carrying out the invention, the water is added in the form of steam. There is advantageously injected into the alkylate a mixture of steam and a gas such as nitrogen which ensures the stirring of the flocculation reactor. The proportion of steam and nitrogen is calculated in such a manner that no free water appears in the flocculator. It thus depends on the temperature of the flocculator. In order to minimize the flow-rate of the nitrogen it may be necessary to operate at a temperature of the order of 50° C for example.

Under these conditions, the salts flocculate in a remarkable manner and the flocculated salts decant readily.

After decantation, there is obtained at the bottom of the column an effluent rich in salt which can be treated by centrifuging and then filtration, while at the head the effluent contains no more salts.

The method according to the invention can be applied to all alkylation processes in the presence of aluminum chloride, in which the nature of the alkylates is compatible with treatment with ammonia. It can be applied to alkylates neutralized with anhydrous ammonia, and also to mixtures of alkylates and residues of catalysts, and in particular to catalytic complexes from an alkylation reaction in the presence of aluminum chloride (red oil) in suspension in an aromatic hydrocarbon medium, preferably the acid alkylate.

The Applicants have in fact discovered that these red oils could be neutralized by energetically dispersing them in one or more aromatic hydrocarbons, and effecting their neutralization by gaseous ammonia with vigorous stirring.

The following examples are given by way of illustration of the invention.

EXAMPLE 1

Neutralization of the Catalytic Complex

The alkylate is coming from a reactor manufacturing ethyl-benzene, in which the benzene is alkylated by ethylene in the presence of aluminum chloride and ethyl chloride, used as a promoter.

At the outlet of the alkylation reactor, there is obtained 50 liters/hr. of acid alkylate containing 60 ml of dissolved complex, and an oily complex phase of which 100 ml/hr. is purged, the remainder being recycled to the alkylation reactor. The mixture of alkylate and purged complex is treated in a tubular neutralizer of 5 cm in diameter and 100 cm in height, stirred by a circulating pump with an output of 300 liters/hr. The mixture of purged complex and alkylate is injected at the level of the pump rotor. At the bottom of the neutralizer there are introduced 200 normal liters of ammonia per hour; the excess ammonia is collected at the head of the neutralizer and the alkylate is distilled in order to extract the ethyl-benzene.

Under these conditions, the catalyst is completely decomposed into ammonium chloride and a salt resulting from the combination of $AlCl_3$ and $NH_3$. The operation is reliable, and no deposit is observed on the reactor walls, even after several months continuous working.

EXAMPLE 2

This example shows that it is possible to work with larger flow-rates and at much greater concentrations of complexes.

The operation is carried out as in Example 1, in the same neutraliser and with the same stirring pump. The flow-rates are as follows:

Flow-rate of alkylates: 50 l/hr. containing 60 cm³ of dissolved complex

Flow-rate of free complex: 2.5 l/hr.

Flow rate of ammonia: 2000 l/hr.

The same results are obtained as in the previous example.

EXAMPLE 3

Separation of the Salts

The operation is the same as for Example 1. 40 kg./hr. of the neutralized alkylate are introduced into a flocculator constituted by a tubular reactor of 5 cm in diameter and 60 cm in height. The alkylate contains 0,5% by weight of salts.

In the lower part of the flocculator there are introduced 200 normal liters per hour of hot nitrogen in which 35 ml/hr. of water has been vaporized. The temperature of the stream of nitrogen is such that the flocculator is kept at a temperature comprised between 50° and 60° C.

The alkylate thus treated is introduced into a decantation tank. At the bottom of this decantation tank there is collected a liquid in which the flocculated salts are five times more concentrated than in the initial alkylate. This mixture is treated in a continuous contrifugal machine. At the outlet of the centrifugal machine there are obtained on the one hand a clarified alkylate containing no more than a few multiples of ten ppm of salts, and on the other hand, a sludge. This sludge is dried and there is recovered the ammonia which is recycled to the neutraliser, and also hydrocarbons which are also recycled.

The decanted alkylate passing out of the upper part of the decanter contains no more salts and is mixed with the clarified alkylate and then filtered and finally degassed in a column with total reflux. The ammonia is recycled to the neutralizer.

It will furthermore be understood that the present invention has been described only by way of explanation and not in any limitative sense, and that any useful modification may be made thereto without thereby departing from its scope.

Thus, it is possible to add the alkylate passing out of the upper part of the decanter to the already-filtered clarified alkylate from the flocculator, or even to eliminate the filter entirely, while maintaining working without incidents for at least several weeks.

We claim:

1. In a method of alkylation of an aromatic hydrocarbon by an olefin hydrocarbon in the presence of aluminum chloride followed by neutralization of the acid alkylates by anhydrous ammonia, the improvement comprising continuously flocculating in the absence of free water the mineral salts obtained by said neutralization by the addition of steam, and separating-out the salts thus flocculated.

2. A method as claimed in claim 1, in which a flow of inert gas is utilized to introduce the steam into said flocculator.

3. A method as claimed in claim 2, in which the quantity of steam added is approximately 15 to 20% of the salts to be flocculated.

4. A method as claimed in claim 2 in which said flocculation is carried out at a sufficient temperature and the proportion of steam and nitrogen is selected to prevent condensation of free water.

5. A method in accordance with claim 1 wherein said neutralization is carried out in a flocculation reactor maintained at about 50°–60° C., said steam being injected into said reactor with nitrogen, the proportion of steam and nitrogen being selected to prevent the occurrence of free water in said reactor.

6. In a method of alkylation of an aromatic hydrocarbon by an olefin hydrocarbon in the presence of aluminum chloride, the steps of (a) neutralization of the catalytic complex comprising aluminum chloride and hydrochloric acid resulting from said alkylation, said complex further containing aromatic hydrocarbons and alkylaromatics, by uniform dispersion of said complex in an aromatic hydrocarbon medium, followed by treatment with gaseous ammonia in slight excess with powerful stirring; (b) flocculation of the salts formed during the course of said neutralization by addition of steam with absence of free water; (c) separation of said salts; and (d) recovery of the alkylate.

7. A method as claimed in claim 6, in which said aromatic hydrocarbon medium is the acid alkylate, and the neutralization of said alkylate is effected simultaneously with that of said complex.

8. A method as claimed in claim 6, in which said olefin hydrocarbon is ethylene and the aromatic hydrocarbon is benzene.

9. A method as claimed in claim 6, in which the said olefin hydrocarbon is propylene and the aromatic hydrocarbon is benzene.

* * * * *